United States Patent [19]

Flug

[11] Patent Number: 5,049,145
[45] Date of Patent: Sep. 17, 1991

[54] DIAPER COVER AND DIAPER WITH SELF CLOSURE HOOK AND LOOP FASTENERS

[75] Inventor: Rachael Flug, Granada Hills, Calif.

[73] Assignee: Diaperaps Limited, Northridge, Calif.

[21] Appl. No.: 645,112

[22] Filed: Jan. 24, 1991

[51] Int. Cl.$^5$ ............................................. A61F 13/62
[52] U.S. Cl. ................................. 604/391; 604/385.1; 24/442
[58] Field of Search ................. 604/385.1, 385.2, 391; 24/442, 444, 447, 452; 128/DIG. 15

[56] References Cited

U.S. PATENT DOCUMENTS

| | | | |
|---|---|---|---|
| 3,541,608 | 11/1970 | Otwell | 128/DIG. 15 X |
| 3,955,575 | 5/1976 | Okuda | 128/DIG. 15 X |
| 4,537,591 | 8/1985 | Coates | 604/391 |
| 4,680,030 | 7/1987 | Coates | 604/391 |
| 4,681,581 | 7/1987 | Coates | 604/391 |
| 4,704,117 | 11/1987 | Mitchell | 604/391 |
| 4,961,736 | 10/1990 | McCloud | 604/385.1 |
| 4,963,140 | 10/1990 | Robertson et al. | 604/389 |

FOREIGN PATENT DOCUMENTS

| | | | |
|---|---|---|---|
| 0256718 | 2/1988 | European Pat. Off. | 24/442 |
| 1276791 | 10/1960 | France | 128/DIG. 15 |
| 2552640 | 4/1985 | France | 24/442 |
| 86/06641 | 11/1986 | World Int. Prop. O. | 128/DIG. 15 |

Primary Examiner—Randall L. Green
Assistant Examiner—David H. Willse
Attorney, Agent, or Firm—Thomas I. Rozsa

[57] ABSTRACT

A diaper or diaper cover with novel self closure hook and loop fasteners. The diaper or diaper cover comprises a piece of fabric, at least one closing member, at least one covering member, and attaching means for attaching one end of the covering member onto the surface of the piece of fabric adjacent to the closing member. The closing and the covering member have respective complementary hook and loop mating surfaces. The covering member may be made of memory retaining resilient foam material having spring effect. The attaching means has a hinge effect on the covering member which combined with the spring effect of the foam material serves to cause mating surface of the covering member to contact and thereby cover the mating surface of the closing member.

72 Claims, 2 Drawing Sheets

DIAPER COVER AND DIAPER WITH SELF CLOSURE HOOK AND LOOP FASTENERS

BACKGROUND OF THE INVENTION

1. Field of the Invention

The present invention relates to the field of diaper covers which are worn around the outside of diapers by babies. The present invention also relates to diapers. The present invention relates in particular to industrial diaper covers and diapers which undergo constant and repeated washing in large numbers during a single wash. In particular, the present invention relates to a novel self closure means to cover the fastening means on the diaper cover or diaper while the diaper cover or diaper is being washed.

2. Description of The Prior Art

There are numerous types of diaper covers and diapers with different kinds of fastening means well known in the prior art. Non-sharp fastening means are commonly used in most types of diaper covers and diapers because the likelihood of a wearer being accidentally injured is substantially reduced. One of the most popular non-sharp fastening means used for the diaper covers in the market today is the VELCRO-R like fastener.

A typical VELCRO-R like fastener comprises a male VELCRO-R like closing member and a female VELCRO-R like closing member. A male VELCRO-R like closing member is often a mating strip with a surface made by filamentary hook type attachment material. A female VELCRO-R like closing member is often a mating strip with a surface made by filamentary loop type or brushed nylon type attachment material. When the two complementary closing members are closed together, they are fastened to each other to serve as a fastener.

However there have been some problems in using hook and loop fasteners on a garment which is frequently washed such as a diaper cover or diaper and especially an industrial diaper cover or diaper. In a situation where a diaper cover with hook and loop fasteners is thrown into a laundering machine, especially when dealing with industrial diaper covers where a large quantity of diaper covers with hook and loop fasteners are thrown into a laundering machine, it is very likely that one closing member of one diaper cover is going to close onto another complementary closing member either of the same diaper cover or of a different one. In either case it will somewhat at least partially close the diaper covers involved which prevent them from being properly cleaned. In addition, male hook closing members, even if they are not closed onto the loop closing members, still have a very good chance to collect lint onto their own surfaces in the washing process and that will greatly reduce their usefulness in the future.

U.S. Pat. No. 4,537,591 issued to Coates on Aug. 27, 1985 for "Adjustable Diaper With A Backband And Fastening Protection Means" discloses a conventional washable adjustable size diaper with VELCRO-R fastening means. The concept of this invention is very much related to an adjustable size diaper which requires the diaper to be substantially rectangular in shape. Nevertheless it also discloses the use of VELCRO-R fastener means. The VELCRO-R fastening means comprises a pair of male VELCRO-R closing tabs attached to the edges of two corners of the diaper respectively and several female VELCRO-R closing strips attached onto the outer side of the diaper adjacent to an opposite edge respectively for adjustable size. It further comprises a pair of female VELCRO-R covering strips attached also to the edges adjacent to the male VELCRO-R closing strips. The male VELCRO-R closing strips may be closed onto the female VELCRO-R closing strips when the diaper is in use, and the female VELCRO-R covering strips may be closed onto the male VELCRO-R closing strips when the diaper is being washed.

U.S. Pat. No. 4,681,581 issued to Coates on July 21, 1987 for "Adjustable Size Diaper And Folding Method Therefor" also discloses an adjustable size diaper with VELCRO-R fastening means. There is also an invention related to an adjustable size diaper and folding methods which takes advantage of a special design of attaching a female VELCRO-R closing bar in the inner side of the diaper adjacent to an edge of the diaper so that when part of the diaper is folded outwardly for adjusting size, the female VELCRO-R like closing bar would face outwardly for fastening. In order to be able to adjust the size, there is adjustment along with a primary fastening means for fastening the diaper to a wearer. The primary fastening means is VELCRO-R fasteners, and the additional fastening means may be snaps or VELCRO-R fasteners. Extra female VELCRO-R covering members are also used for covering the male VELCRO-R closing members in laundering.

There were some similarities in the VELCRO-R fastening means in the above inventions. The female VELCRO-R closing strips were attached adjacent to one edge of the diaper. The male VELCRO-R like closing strips were attached adjacent to the corners at another opposite edge of the diaper. The way the male VELCRO-R closing strip is attached is to have one end of the strip free-floating and the other end attached to the corner edge of the diaper. In the same way the female VELCRO-R covering strips are attached to the diaper adjacent to the male VELCRO-R closing strips respectively. However there are some disadvantages to this type of attaching means. One disadvantage is that when the male VELCRO-R closing strips close onto the female VELCRO-R closing strips, all the strength applied on the male VELCRO-R closing strips will be transferred on the connecting point at the corner edge of the diaper. It is well known that the edge of clothing is very easily damaged in wearing and washing and having the fastening strips attached to it will definitely increase the chances of tearing it off. Therefore having fastening means attached to the corner edge of a diaper or diaper cover reduces the reliability and durability of the diaper. Another disadvantage of having only one end of the VELCRO-R strips attached to the edge of a diaper is that since they stick out from the edge of the diaper without any further support they tend to become wrinkled, warped and deteriorated because of the extended exposure to the high temperature and harsh chemicals in laundering.

U.S. Pat. No. 4,680,030 issued to Coates on July 14, 1987 for "Garment Having Improved, Self Closing, Filamentary Fasteners" discloses a diaper where at least two pieces of fabric have been used for the purpose of having the male VELCRO-R closing strips and the female VELCRO-R covering strips completely attached onto respective pieces of fabric. Instead of one end of the male VELCRO-R closing strip and the female VELCRO-R covering strip being freefloating, one end of the piece of fabric on which the female VELCRO-R covering strip is attached is free-floating.

The above invention provided one approach to preventing the VELCRO-R strips from being wrinkled and warped during laundering. However this approach has a few drawbacks. One drawback is that it uses more fabric materials which eventually increase the cost of the diaper. Another drawback is that when the diaper is worn, the piece of fabric which has a free-floating end is folded inward, therefore the thickness at that part of the diaper is doubled which reduces the comfort for the baby and further makes it awkward to use.

It will be very useful to have garments such as diaper covers and diapers with VELCRO-R or hook and loop fasteners which are self-closing to prevent lint accumulation on the hook member. In addition, such members are fully supported by the garment to prevent wrinkling and warping and further resist deterioration, all without necessitating the use of extra material. Such diaper or diaper covers will be very reliable yet comfortable to wear. The hook and loop closing members will prevent the standard diaper or diaper cover from closing so that the entire diaper or diaper cover can be effectively washed.

SUMMARY OF THE PRESENT INVENTION

The present invention is a diaper cover and a diaper with novel self closure hook and loop fasteners.

It is known that VELCRO-R fasteners, or hook and loop fasteners may be used for a garment such as a diaper cover or diaper as a non-sharp fastening means which reduces the possibility of accidentally injuring the wearer. To prevent the lint accumulation on the hook closing members during the laundering, loop covering members have been added to cover the hook closing members for protection. To prevent the wrinkling, warping and deterioration of the hook closing members and the loop covering members, additional pieces of fabric have been added to completely attach the hook closing members and the loop covering members onto a respective piece of fabric so that during laundering the hook closing members and the loop covering members are fully supported by respective pieces of fabric.

It has been discovered, according to the present invention, that for a diaper cover or diaper having a piece of fabric as its main part, it is necessary to have the male VELCRO-R or hook closing member completely attached onto one side of the piece of fabric, not to attach only one end of the male VELCRO-R or hook closing member to an edge of the piece of fabric, to not only prevent wrinkling, warping and deterioration of the male VELCRO-R or hook closing members during laundering, but also to protect the tearing off and damage at the edge of the piece of fabric and increase the reliability and durability of the diaper cover.

It has been further discovered, according to the present invention, that when a female VELCRO-R or loop covering member is attached onto the same piece of fabric adjacent to the male VELCRO-R or hook closing member in a way as shown in FIG. 2 where one end of the female VELCRO-R or loop covering member is free-floating and the other end is sewn onto the same piece of fabric with double stitch lines along the inside end of the male VELCRO-R or hook closing member and the complementary VELCRO-R surfaces of both members are facing each other, the female VELCRO-R or loop covering member will to tend to close onto the male VELCRO-R or hook closing member. Therefore the above described means of double stitch line sewing has a hinge or spring effect which causes the female VELCRO-R or loop covering member to close onto the male VELCRO-R or hook closing member and is well served as a self closure mechanism for the purpose of protecting the male VELCRO-R or hook closing member from lint accumulating during laundering and further prevent the male VELCRO-R or hook closing member from attaching to the female VELCRO-R or loop closing member and thereby cause a portion of the diaper or diaper cover to be closed during washing.

It has additionally been discovered, according to the present invention, that it is not necessary to add an additional piece of fabric for the purpose of completely creating a closing means of both the male VELCRO-R or hook closing member and the female VELCRO-R or loop covering member. With the male VELCRO-R or hook closing member completely attached to and fully supported by a piece of fabric, the female VELCRO-R or loop covering member is also fully supported once it is self-closed onto the male VELCRO-R or hook closing member. Only one piece of fabric is needed to provide full support to both the male VELCRO-R or hook closing member and the female VELCRO-R or loop covering member.

It is therefore an object of the present invention to provide a diaper cover or diaper with self closure hook and loop fasteners comprising an attaching means which has a hinge or spring effect on a loop covering member and causes the loop covering member to be self-closed onto a hook closing member to protect the hook closing member from damages such as lint buildup in laundering and from closing onto its normal loop closing member at a remote location on the diaper cover or diaper, or attaching itself to other diapers.

It is a further object of the present invention to provide a diaper cover or diaper with self closure hook and loop fasteners wherein the hook closing member is completely attached to the diaper cover for full support to ensure the reliability and durability of wearing the diaper cover and to prevent the wrinkling, warping and deterioration of the hook closing members in laundering.

It is an additional object of the present invention to provide a diaper cover or diaper with a self closure hook and loop fasteners which also prevent the wrinkling, warping and deterioration of the loop covering members by the selfclosing feature without having the loop covering member completely attached to a piece of fabric, thereby eliminating the use of an additional piece of fabric.

It is also an object of the present invention to provide a diaper cover or diaper with self closure hook and loop fasteners comprising an attaching means which has a hinge spring effect on a hook covering member and causes the hook covering member to be self-closed onto a loop closing member to protect the loop closing member from damage and further to prevent it from closing onto its normal hook closing member at a remote location on the diaper cover or diaper.

It is a further object of the present invention to provide a diaper cover or diaper with self closure hook and loop fasteners wherein the loop closing member is completely attached to the diaper cover for full support to insure the reliability and durability of wearing the diaper cover and to prevent the wrinkling, warping and deterioration of the loop closing member in laundering.

It is an additional object of the present invention to provide a diaper cover or diaper with self closure hook and loop fasteners which also prevent the wrinkling, warping and deterioration of the hook covering member by the selfclosing feature without having the hook covering member completely attached to a piece of fabric, thereby eliminating the use of an additional piece of fabric.

It is another object of the present invention to create a self closure fastener which is easy to use.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the invention. Various changes and modifications obvious to one skilled in the art to which the invention pertains are deemed to be within the spirit, scope and contemplation of the invention as further defined in the appended claims.

Figure 1:
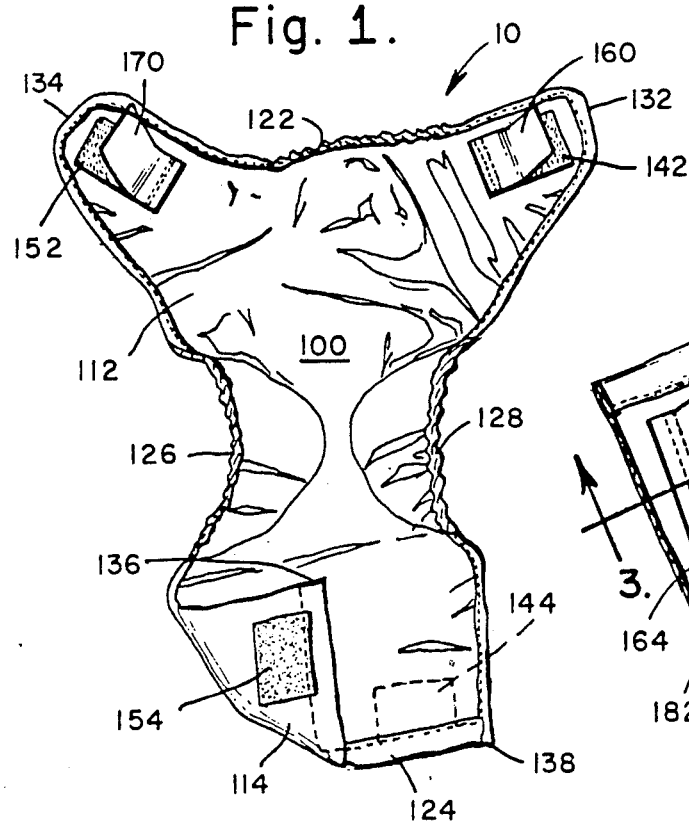
FIG. 1 is a perspective view of the present invention diaper cover or diaper with self closure hook and loop fasteners, where two hook closing members are affixed spaced apart to the inner surface of the diaper cover or diaper adjacent to one end, two corresponding loop closing members are affixed spaced apart to the outer surface of the diaper cover or diaper adjacent to the opposite end, and two loop diaper cover or diaper adjacent to the two hook closing members respectively.

Referring to FIG. 1, there is shown a diaper cover or diaper 10 which incorporates one preferred embodiment of the present invention. A piece of fabric 100 has an inner surface 112 and an outer surface 114. The piece of fabric 100 is generally saddle shaped with a curved end 122, a generally straight end 124, and two oppositely disposed recessed edges 126 and 128. At end 122 of the piece of fabric 100 there are two outwardly extending corners 132 and 134. At opposite end 124 of the piece of fabric 100 there are two corners 136 and 138. The piece of fabric 100 is preferably a multi-layer fabric if it is a diaper cover having the properties such as being non-permeable to liquid but permeable to air. Alternatively, the piece of fabric 100 can be a single layer fabric which is both nonpermeable to liquid and to air.

Two hook closing members 142 and 152 both having a respective hook mating surface are completely sewn onto inner surface 112 of the piece of fabric 100 adjacent to corners 132 and 134 respectively with their hook mating surfaces exposed. Two loop closing members 144 and 154 both having a respective loop mating surface are completely sewn onto outer surface 114 of the same piece of fabric 100 adjacent to corners 138 and 136 respectively with their loop mating surfaces exposed. Two loop covering members 150 and 160 both having a respective loop mating surface are also attached to inner surface 112 of the same piece of fabric 100 adjacent to the two hook closing members 142 and 152 respectively.

Figure 2:
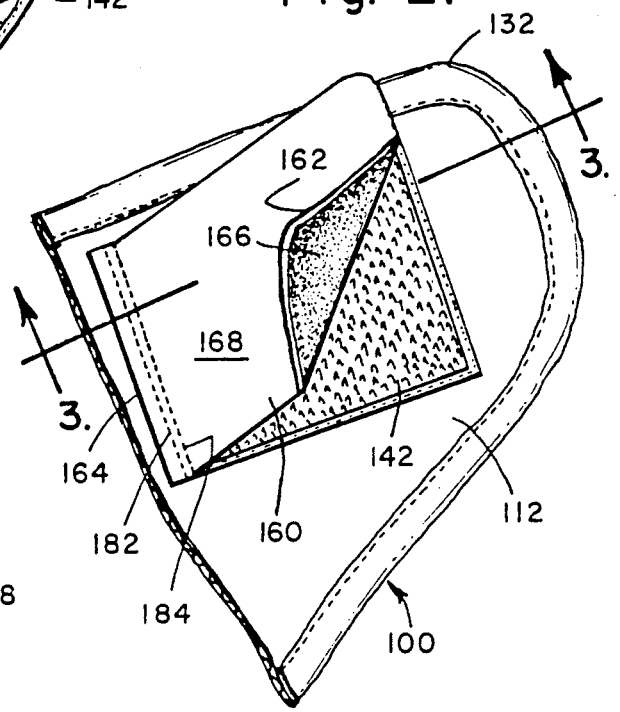
FIG. 2 is an enlarged view of the corner part of a preferred embodiment of the present invention diaper cover or diaper with self closure hook and loop fasteners, where the hook closing member is affixed to the inner surface of the diaper cover or diaper, and the loop covering member is attached to the inner surface of the diaper cover or diaper adjacent to the hook closing member by a pair of spaced apart stitch lines.
Figure 3:
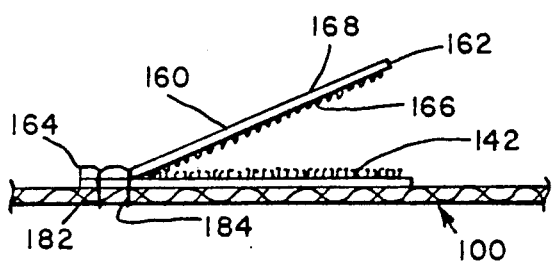
FIG. 3 is a cross-sectional view taken along line 3—3 of FIG. 2.

Referring to FIG. 2 and FIG. 3, there is shown a detailed perspective view, along with a cross-sectional view, of corner 132. Hook closing member 142 is completely sewn onto inner surface 112 of the piece of fabric 100 adjacent to corner 132 with its hook mating surface exposed. Loop covering member 160 is attached to the same surface of the piece of fabric 100 where hook closing member 142 is sewn onto. Loop covering member 160 is preferably made of a memory retaining foam. The traditional single VELCRO-R fastening tab used in prior art usually will crumble and deteriorate from numerous industrial washings and will not hold up to frequent washing with chlorine and similar detergents. In one of the preferred embodiments of the present invention, one side of the memory retaining foam is laminated to have a loop mating surface. In one of the alternative embodiments of the present invention that side of the memory retaining foam is sewn to have a loop mating surface. The other side of the memory retaining foam is laminated to strengthen the foam so it will not crumble and deteriorate from numerous industrial washing and will hold up to frequent washing with chlorine and similar detergents. The lamination is of course optional. Loop covering member 160 has two sides 166 and 168. Side 166 is the side of the memory retaining foam which has the loop mating surface, and it is facing the hook mating surface of hook closing member 142. It needs to be emphasized that this is merely one embodiment of the present invention. Other types of material with loop mating surface may also be employed, such as female VERCRO-R type material or materials with filamentary loop type surface or the like, and are also within the scope and spirit of the present invention. Loop covering member 160 has two ends 162 and 164. End 162 is free-floating. The other end 164 is sewn onto the piece of fabric 100 with two spaced apart parallel stitch lines 182 and 184 to produce a hinge or spring effect on the loop covering member 160 so it tends to close onto hook closing member 142. By way of example only, the two parallel stitch lines 182 and 184 are preferably approximately ¼ inch apart. The combination of the loop covering member 160 being made of a memory retaining foam, combined with the two parallel and spaced apart stitch lines 182 and 184 which create a hinge effect, serves to provide a very effective self closure means to cover hook closing member 142. The material is also soft and light weight, thereby not providing discomfort to the baby while the diaper cover is worn.

It will be appreciated that hook closing member 152 and loop covering member 170 at corner 134 have the same configuration. Also in the embodiments illustrated, the stitched end of loop covering member 160 is closer to the center of the piece of fabric 100 while the free-floating end is closer to the corner. It will be appreciated that the stitched end of loop covering member 170 is closer to the edge of the piece of fabric 100, so that the free-floating end is closer to the center.

When the diaper cover or diaper 10 is worn by a baby, loop covering members 160 and 170 are opened away from hook closing members 142 and 152 respectively, and hook closing members 142 and 152 are closed onto loop closing members 144 and 154 respectively. Hook closing members 142 and 152 are completely sewn onto the inner surface of the piece of fabric 100 so the strength is not applied at the edge of the piece of fabric 100 which substantially increases the reliability and durability of the diaper cover or diaper 10.

When the diaper cover 10 or diaper is not worn and hook closing members 142 and 152 are opened away from loop closing members 144 and 154 respectively, loop covering members 160 and 170 will be self-closed onto hook closing members 142 and 152 respectively which prevents damage on hook closing members 142 and 152 such as lint accumulation.

When the diaper cover 10 is washed, hook closing members 142 and 152 and loop covering members 160 and 170 will not be wrinkled, warped and deteriorated because hook closing members 142 and 152 are fully supported by the piece of fabric 100 and loop covering members 160 and 170 are self-closed onto hook closing members 142 and 152 respectively.

Most important, through the self-closing feature of the loop covering members 160 and 170 closing the hook closing members 142 and 152, the hook closing members 142 and 152 will not close onto loop closing members 144 and 154 respectively, so there is no portion of diaper cover or diaper 10 that will be covered by such closure, which in turn provides that diaper cover or diaper 10 can be more promptly and completely washed. In addition, the hook closing members 142 and 152 will not attach to the loop closing members of adjacent diapers or diaper covers. Therefore, the entire piece of fabric 100 of the diaper cover or diaper 10 is exposed for washing.

Figure 4:
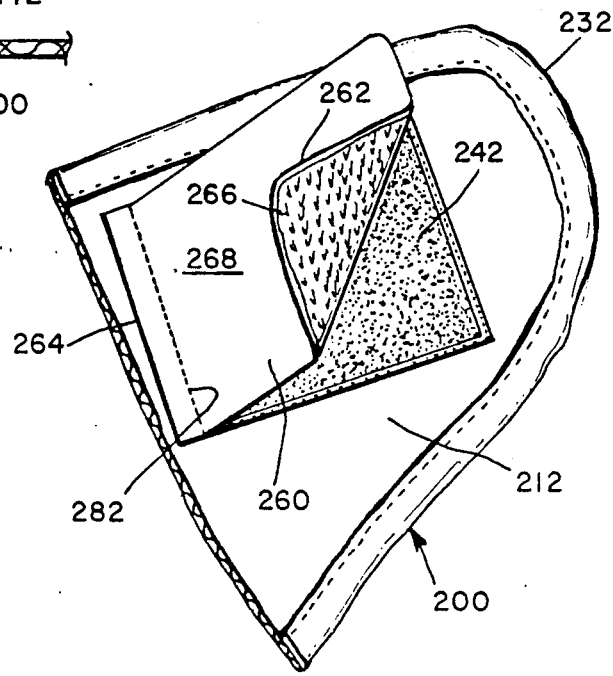
FIG. 4 is an enlarged view of the corner part of an alternative embodiment of the present invention diaper cover or diaper with self closure hook and loop fasteners, where the loop closing member is affixed to the inner surface of the diaper cover or diaper, and the hook covering member is attached to the inner surface of the diaper cover or diaper adjacent to the loop closing member.

An enlarged view of one of the alternative embodiments of the present invention diaper cover and diaper with self closure means fasteners is illustrated in FIG. 4. In this embodiment the hook and loop types are reversed for all closing and covering members. As shown in FIG. 4, loop closing member 242 is now completely sewn onto the inner surface of the fabric, and hook covering member 260 is attached to the inner surface of the same piece of fabric adjacent to the loop closing member 242. It will be appreciated that other features and options discussed for diaper cover or diaper 10 are also applied here. FIG. 4 also shows an alternation where one end 264 of covering member 260 is affixed to the piece of fabric by only one stitch line 282. Of course it can also be affixed by double stitch lines. It is emphasized that other stitching methods may also be employed for the various embodiments of the present invention, such as a triple line stitch pattern, a narrow rectangular stitch pattern, and so on.

Figure 5:
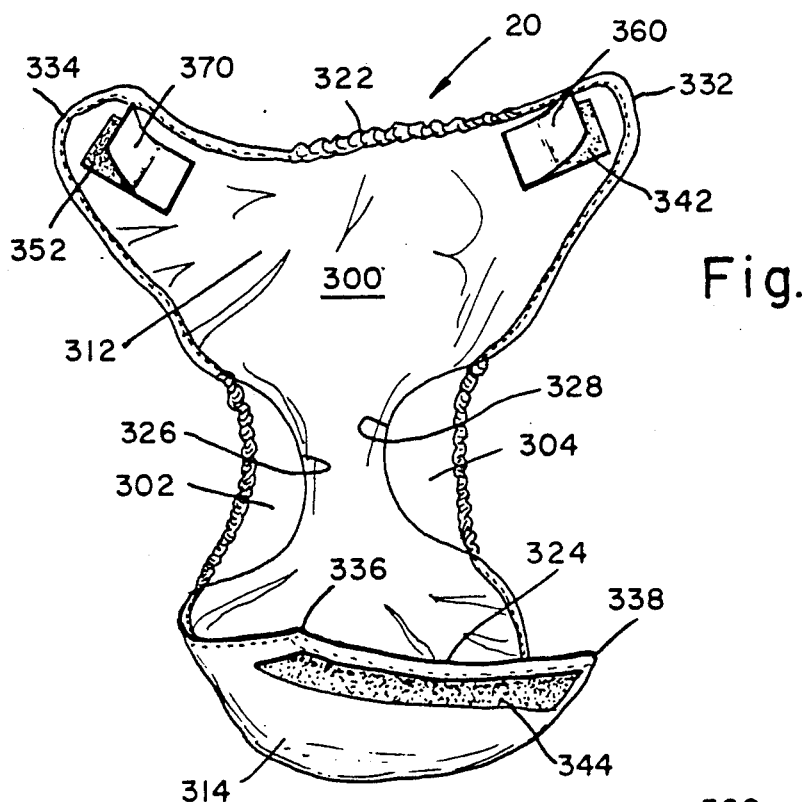
FIG. 5 is a perspective view of another preferred embodiment of the present invention diaper cover or diaper with self closure hook and loop fasteners, where two hook closing members are affixed spaced apart to the inner surface of the diaper cover or diaper adjacent to one end, one corresponding loop closing member is affixed to the outer surface of the diaper cover or diaper adjacent to the opposite end, and two loop covering members are attached to the inner surface of the diaper cover or diaper adjacent to the two hook closing members respectively. There are also two gussets affixed at two oppositely disposed edges of the diaper cover or diaper respectively.

Referring to FIG. 5, there is shown a diaper cover or diaper 20 which incorporates another preferred embodiment of the present invention. A piece of fabric 300 again has an inner surface 312 and an outer surface 314. The piece of fabric 300 is generally saddle shaped with a curved end 322, a generally straight end 324, and two oppositely disposed recessed edges 326 and 328. Two gussets 302 and 304 are now attached to recessed edges 326 and 328 respectively to further prevent leakage, which provides another important advantage of the present invention. At end 322 of the piece of fabric 300 there are two outwardly extending corners 332 and 334. At opposite end 324 of the piece of fabric 300 there are two corners 336 and 338. The piece of fabric 300 is preferably a multi-layer fabric if it is a diaper cover having the properties such as being non-permeable to liquid but permeable to air. Alternatively, the piece of fabric 300 can be a single layer fabric which is both nonpermeable to liquid and to air. Gussets 302 and 304 may be made of the same material as the piece of fabric 300.

Two hook closing members 342 and 352 both having a respective hook mating surface are completely sewn onto inner surface 312 of the piece of fabric 300 adjacent to corners 332 and 334 respectively with their hook mating surfaces exposed. One bar shaped loop closing member 344 having a loop mating surface is completely sewn onto outer surface 314 of the same piece of fabric 300 adjacent to end 324 with its loop mating surface exposed. Two loop covering members 360 and 370 both having a respective loop mating surface are also attached to inner surface 332 of the same piece of fabric 300 adjacent to the two hook closing members 342 and 352 respectively.

Figure 6:
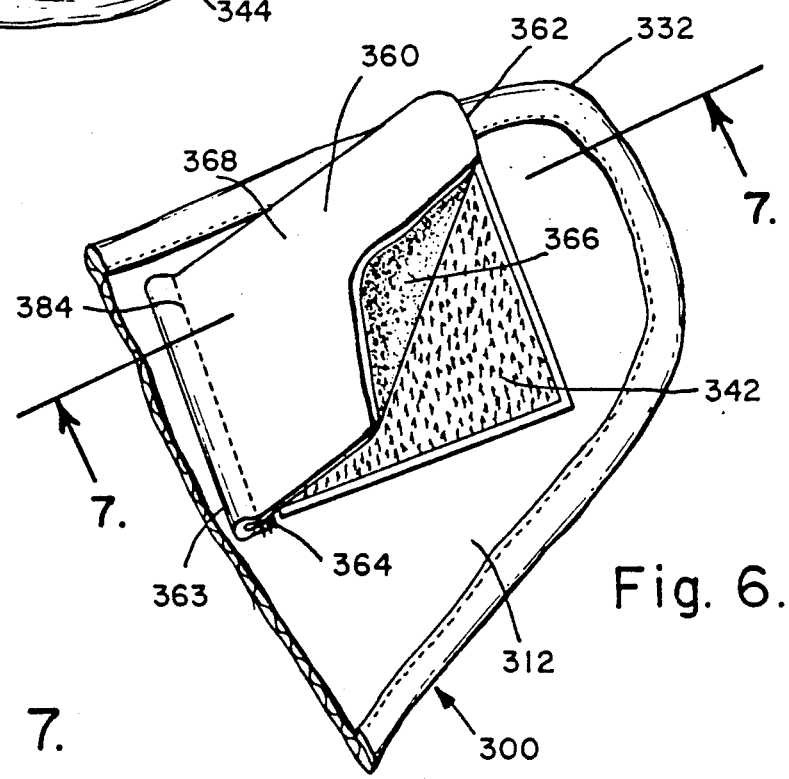
FIG. 6 is an enlarged view of the corner part of the other preferred embodiment of the present invention diaper cover or diaper with self closure hook and loop fasteners, where the hook closing member is affixed to the inner surface of the diaper cover or diaper, and the loop covering member is attached to the inner surface of the diaper cover or diaper adjacent to the hoop closing member, with its end folded underneath towards the hook closing member.
Figure 7:
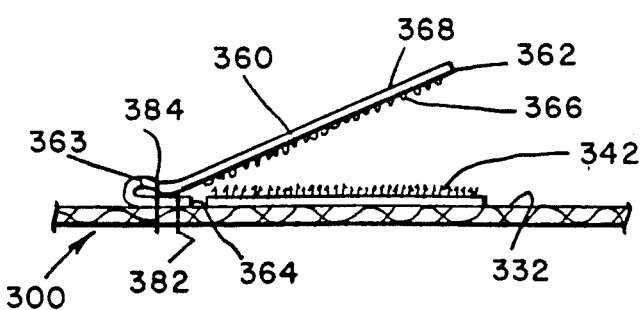
FIG. 7 is a cross-sectional view taken along line 7—7 of FIG. 6.

Referring to FIG. 6 and FIG. 7, there is shown a detailed perspective view, along with a cross-sectional view, of corner 332. Hook closing member 342 is completely sewn onto inner surface 332 of the piece of fabric 300 adjacent to corner 332 with its hook mating surface exposed. Loop covering member 360 is attached to the same surface of the piece of fabric 300 onto which hook closing member 342 is sewn. Loop covering member 360 is also preferably made of the memory retaining foam discussed earlier. Loop covering member 360 has two sides 366 and 368. Side 366 is the side of the memory retaining foam which has the loop mating surface, and it is facing the hook mating surface of hook closing member 342. It again needs to be emphasized that this is merely one embodiment of the present invention and other types of material with a loop mating surface may also be employed. Loop covering member 360 has two ends 362 and 364. End 362 is free-floating. The difference between this embodiment and the previously disclosed embodiments, is the way of sewing the other end 364 onto the piece of fabric 300. A small portion of end 364 of loop covering member 360 is folded along line 363 underneath and sewn to the piece of fabric 300 first by a single stitch line 382 parallel to the folding line 363. After being folded, it is stitched again with another stitch line 384 parallel to the folding line 363. This is best shown in FIG. 7. Of course stitch line 382 may be eliminated, or it may also be stitched all the way through as stitch line 384 does. More stitch lines or other stitch patterns may also be used to enhance the attachment and hinge effect. The combination of the loop covering member 360 which is made of a memory retaining foam, combined with the folding at end 364 which also creates a hinge effect serves to provide a very effective self closure means to cover hook closing member 342.

It will be appreciated that hook closing member 352 and loop covering member 370 at corner 334 have the same configuration. Also in the embodiments illustrated, the stitched end of loop covering member 360 is closer to the center of the piece of fabric 300 while the free-floating end is closer to the corner. It will be appreciated that the stitched end of loop covering member is closer to the edge of the piece of fabric 300, so that the free-floating end is closer to the center.

It is again emphasized that other stitching methods may also be employed for the various embodiments of the present invention, such as a triple line stitch pattern, a narrow rectangular stitch pattern, and so on. The covering members of the present invention are preferably made of a memory retaining foam material which by itself already has a self closure feature. Therefore simpler means of affixing the covering members to the diaper covers or diapers may also be employed in some embodiments of the present invention without departing from the spirit and scope of the present invention.

Defined in detail, the present invention is a diaper cover comprising: (a) a fabric having a surface and an edge; (b) a first hook closing member having a hook mating surface, where the first hook closing member is nonnonmovably affixed onto the surface of said fabric at a first location adjacent to the edge of said fabric, such that the hook mating surface of the first hook closing member faces away from the surface of said fabric; (c) a second hook closing member having a hook mating surface, where the second hook closing member is nonmovably affixed onto the surface of said fabric at a second location adjacent to the edge of said fabric and remote from said first hook closing member, such that the hook mating surface of the second hook closing member faces away from the surface of said fabric; (d) a first loop covering member having a loop mating surface and an end attached to the surface of said fabric adjacent to said first hook closing member by a first pair of spaced apart stitch lines, such that the loop mating surface of the first loop covering member faces the hook mating surface of said first hook closing member; and (e) a second loop covering member having a loop mating surface and an end attached to the surface of said fabric adjacent to said second hook closing member by a second pair of spaced apart stitch lines, such that the loop mating surface of the second loop covering member faces the hook mating surface of the second hook closing member; (f) whereby said first and second pairs of spaced apart stitch lines have hinge effect on said first and second loop covering members respectively, which serves to cause the loop mating surface of said first loop covering member to contact and thereby cover the hook mating surface of said first hook closing member, and to cause the loop mating surface of said second loop covering member to contact and thereby cover the hook mating surface of said second hook closing member.

In a preferred embodiment of the present invention, (a) the end of said first loop covering member is attached to the surface of said fabric adjacent to said first hook closing member and remote from the edge of said fabric, and the end of said second loop covering member is attached to the surface of said fabric adjacent to said second hook closing member and remote from the edge of said fabric; (b) the first and second loop covering members are made of memory retaining resilient foam material having spring effect, which combined with the hinge effect of said first and second pairs of stitch lines further serves to cause the loop mating surface of said first loop covering member to contact and thereby cover the hook mating surface of said first hook closing member, and to cause the loop mating surface of said second loop covering member to contact and thereby cover the hook mating surface of said second hook closing member; (c) said memory retaining resilient foam material has a first side and an oppositely disposed second side, where the first side is laminated to have a loop mating surface, and the second side is laminated to protect said memory retaining resilient foam material from being damaged; and (d) the diaper cover further comprises two gussets attached spaced apart to the edge of said fabric to provide additional coverage.

Also defined in detail, the present invention is a diaper cover comprising: (a) a fabric having a surface and an edge; (b) a first hook closing member having a hook mating surface, where the first hook closing member is nonmovably affixed onto the surface of said fabric at a first location adjacent to the edge of said fabric, such that the hook mating surface of the first hook closing member faces away from the surface of said fabric; (c) a second hook closing member having a hook mating surface, where the second hook closing member is nonmovably affixed onto the surface of said fabric at a second location adjacent to the edge of said fabric and remote from said first hook closing member, such that the hook mating surface of the second hook closing member faces away from the surface of said fabric; (d) a first loop covering member having a loop mating surface and a folded end attached to the surface of sad fabric adjacent to said first hook closing member by at least one stitch line, such that the loop mating surface cf the first loop covering member faces the hook mating surface of said first hook closing member and the folded end of the first loop covering member contacts the surface of said fabric; and (e) a second loop covering member having a loop mating surface and a folded end attached to the surface of said fabric adjacent to said second hook closing member by at least one stitch line, such that the loop mating surface of the second loop covering member faces the hook mating surface of said second hook closing member and the folded end of the second loop covering member contacts the surface of said fabric; (f) whereby the attached folded ends of said first and second loop covering members have hinge effect on said first and second loop covering members respectively, which serves to cause the loop mating surface of said first loop covering member to contact and thereby cover the hook mating surface of said first hook closing member, and to cause the loop mating surface of said second loop covering member to contact and thereby cover the hook mating surface of said second hook closing member.

Defined broadly, the present invention is a diaper cover comprising: (a) a fabric having a surface and an edge; (b) a first hook closing member having a hook mating surface, where the first hook closing member is nonmovably affixed onto the surface of said fabric at a first location adjacent to the edge of said fabric, such that the hook mating surface of the first hook closing member faces away from the surface of said fabric; (c) a second hook closing member having a hook mating surface, where the second hook closing member is nonmovably affixed onto the surface of said fabric at a second location adjacent to the edge of said fabric and remote from said first hook closing member, such that the hook mating surface of the second hook closing member faces away from the surface of said fabric; (d) a first loop covering member having a loop mating surface and an end attached to the surface of said fabric adjacent to said first hook closing member, such that the loop mating surfaces of the first loop covering member faces the hook mating surface of said first hook closing member, where the first loop covering member is made of memory retaining resilient material having a spring effect; and (e) a second loop covering member having a loop mating surface and an end attached to the surface of said fabric adjacent to said second hook closing member, such that the loop mating surface of the second loop covering member faces the hook mating surface of the second hook closing member, where the second loop covering member is made of memory retaining resilient material having a spring effect; (f) whereby the spring effect of said memory retaining resilient foam material serves to cause the loop mating surface of said first loop covering member to contact and thereby cover the hook mating surface of said first hook closing member, and to cause the loop mating surface of said second loop covering member to contact and thereby cover the hook mating surface of said second hook closing member.

Defined more broadly, the present invention is a diaper cover comprising: (a) a fabric having a surface and an edge; (b) at least one hook closing member having a hook mating surface, where the a& least one hook closing member is nonmovably affixed onto the surface of said fabric at a location adjacent to the edge of said fabric, such that the hook mating surface cf the at least one hook closing member faces away from the surface of said fabric; and (c) at least one loop covering member having a loop mating surface and an end attached to the surface of said fabric adjacent to said at least one hook closing member by a pair of spaced apart stitch lines, such that the loop mating surface of the at least one loop covering member faces the hook mating surface of said at least one hook closing member; (d) whereby said pair of spaced apart stitch lines has a hinge effect on said at least one loop covering member, which serves to cause the loop mating surface cf said at least one loop cover-ing member to contact and thereby cover the hook mating surface of said at least one hook closing member Also defined more broadly, the present invention is a diaper cover comprising: (a) a fabric having a surface and an edge; (b) at least one hook closing member having a hook mating surface, where the at least one hook closing member is nonmovably affixed onto the surface of said fabric at a location adjacent to the edge of said fabric, such that the hook mating surface of the at least one hook closing member faces away from the surface of said fabric; and (c) at least one loop covering member having a loop mating surface and a folded end attached to the surface of said fabric adjacent to said at least one hook closing member by at least one stitch line, such that the loop mating surface of the at least one loop covering member faces the hook mating surface of said at least one hook closing member and the folded end of the at least one loop covering member contacts the surface of said fabric; (d) whereby the attached folded end of said at least one loop covering members has a hinge effect on said at least one loop covering member, which serves to cause the loop mating surface of said at least one loop covering member to contact and thereby cover the hook mating surface of said at least one hook closing member.

Defined most broadly, the present invention is a diaper cover comprising: (a) a fabric having a surface and an edge; (b) at least one hook closing member having a hook mating surface, where the at least one hook closing member is nonmovably affixed onto the surface of said fabric at a location adjacent to the edge of said fabric, such that the hook mating surface of the at least one hook closing member faces away from the surface of said fabric; and (c) at least one loop covering member having a loop mating surface and an end attached to the surface of said fabric adjacent to said at least one hook closing member, such that the loop mating surface of the at least one loop covering member faces the hook mating surface of the at least one hook closing member, where the at least ore loop covering member is made of memory retaining resilient material having a spring effect; (d) whereby the spring effect of said memory retaining resilient foam material serves to cause the loop mating surface of said at least one loop covering member to contact and thereby cover the hook mating surface of said at least one hook closing member.

Alternatively defined in detail, the present invention is a diaper comprising: (a) a fabric having a surface and an edge; (b) a first hock closing member having a hook mating surface, where the first hook closing member is nonmovably affixed onto the surface of said fabric at a first location adjacent to the edge of said fabric, such that the hook mating surface of the first hook closing member faces away from the surface of said fabric; (c) a second hook closing member having a hook mating surface, where the second hook closing member is nonmovably affixed onto the surface of said fabric at a second location adjacent to the edge of said fabric and remote from said first hook closing member, such that the hook mating surface of the second hook closing member faces away from the surface of said fabric; (d) a first loop covering member having a loop mating surface and an end attached to the surface of said fabric adjacent to said first hook closing member by a first pair of spaced apart stitch lines, such that the loop mating surface of the first loop covering member faces the hook mating surface of said first hook closing member; and (e) a second loop covering member having a loop mating surface and an end attached to the surface of said fabric adjacent to said second hook closing member by a second pair of spaced apart stitch lines, such that the loop mating surface of the second loop covering member faces the hook mating surface of the second hook closing member; (f) whereby said first and second pairs of spaced apart stitch lines have a hinge effect on said first and second loop covering members respectively, which serves to cause the loop mating surface of said first loop covering member to contact and thereby cover the hook mating surface of said first hook closing member, and to cause the loop mating surface of said second loop covering member to contact and thereby cover the hook mating surface of said second hook closing member.

In an alternative embodiment of the present invention, (a) the end of said first loop covering member is attached to the surface of said fabric adjacent to said first hook closing member and remote from the edge of said fabric, and the end of said second loop covering member is attached to the surface of said fabric adjacent to said second hook closing member and remote from the edge of said fabric; (b) the first and second loop covering members are made of memory retaining resilient foam material having spring effect, which combined with the hinge effect of said first and second pairs of stitch lines further serves to cause the loop mating surface of said first loop covering member to contact and thereby cover the hook mating surface of said first hook closing member, and to cause the loop mating surface of said second loop covering member to contact and thereby cover the hock mating surface of said second hook closing member; (c) said memory retaining resilient foam material has a first side and an oppositely disposed second side, where the first side is laminated to have a loop mating surface, and the second side is laminated to protect said memory retaining resilient foam material from being damaged; and (d) the diaper further comprises two gussets attached spaced apart to the edge of said fabric to provide additional coverage.

Alternatively defined also in detail, the present invention is a diaper comprising: (a) a fabric having a surface and an edge; (b) a first hook closing member having a hook mating surface, where the first hook closing member is nonmovably affixed onto the surface of said fabric at a first location adjacent to the edge of said fabric, such that the hook mating surface of the first hook closing member faces away from the surface of said fabric; (c) a second hook closing member having a hook mating surface, where the second hook closing member is nonmovably affixed onto the surface of said fabric at a second location adjacent to the edge of said fabric and remote from said first hook closing member, such that the hook mating surface of the second hook closing member faces away from the surface of said fabric; (d) a first loop covering member having a loop mating surface and a folded end attached to the surface of said fabric adjacent to said first hook closing member by at least one stitch line, such that the loop mating surface cf the first loop covering member faces the hook mating surface of said first hook closing member and the folded end of the first loop covering member contacts the surface of said fabric; and (e) a second loop covering member having a loop mating surface and a folded end attached to the surface of said fabric adjacent to said second hook closing member by at least one stitch line, such that the loop mating surface of the second loop covering member faces the hook mating surface of said second hook closing member and the folded end of the second loop covering member contacts the surface of said fabric; (f) whereby the attached folded ends of said first and second loop covering members have a hinge effect on said first and second loop covering members respectively, which serves to cause the loop mating surface of said first loop covering member to contact and thereby cover the hook mating surface of said first hook closing member, and to cause the loop mating surface of said second loop covering member to contact and thereby cover the hook mating surface of said second hook closing member.

Alternatively defined broadly, the present invention is a diaper comprising: (a) a fabric having a surface and an edge; (b) a first hook closing member having a hook mating surface, where the first hook closing member is nonmovably affixed onto the surface of said fabric at a first location adjacent to the edge of said fabric, such that the hook mating surface of the first hook closing member faces away from the surface of said fabric; (c) a second hook closing member having a hook mating surface, where the second hook closing member is nonmovably affixed onto the surface of said fabric at a second location adjacent to the edge of said fabric and remote from said first hook closing member, such that the hook mating surface of the second hook closing member faces away from the surface of said fabric; (d) a first loop covering member having a loop mating surface and an end attached to the surface of said fabric adjacent to said first hook closing member, such that the loop mating surface of the first loop covering member faces the hook mating surface of said first hook closing member, where the first loop covering member is made of memory retaining resilient material having a spring effect; and (e) a second loop covering member having a loop mating surface and an end attached to the surface of said fabric adjacent to said second hook closing member, such that the loop mating surface of the second loop covering member faces the hook mating surface of the second hook closing member, where the second loop covering member is made of memory retaining resilient material having a spring effect; (f) whereby the spring effect of said memory retaining resilient foam material serves to cause the loop mating surface of said first loop covering member to contact and thereby cover the hook mating surface of said first hook closing member, and to cause the loop mating surface of said second loop covering member to contact and thereby cover the hook mating surface of said second hook closing member.

Alternatively defined more broadly, the present invention is a diaper comprising: (a) a fabric having a surface and an edge; (b) at least one hook closing member having a hook mating surface, where the at least one hook closing member is nonmovably affixed onto the surface of said fabric at a location adjacent to the edge of said fabric, such that the hook mating surface of the at least one hook closing member faces away from the surface of said fabric; and (c) at least one loop covering member having a loop mating surface and an end attached to the surface of said fabric adjacent to said at least one hook closing member by a pair of spaced apart stitch lines, such that the loop mating surface of the at least one loop covering member faces the hook mating surface of said at least one hook closing member; (d) whereby said pair of spaced apart stitch lines has a hinge effect on said at least one loop covering member, which serves to cause the loop mating surface of said at least one loop covering member to contact and thereby cover the hook mating surface of said at least one hook closing member.

Alternatively defined also more broadly, the present invention is a diaper comprising: (a) a fabric having a surface and an edge; (b) at least one hook closing member having a hook mating surface, where the at least one hook closing member is nonmovably affixed onto the surface of said fabric at a location adjacent to the edge of said fabric, such that the hook mating surface of the at least one hook closing member faces away from the surface of said fabric; and (c) at least one loop covering member having a loop mating surface and a folded end attached to the surface of said fabric adjacent to said at least one hook closing member by at least one stitch line, such that the loop mating surface of the at least one loop covering member faces the hook mating surface of said at least one hook closing member and the folded end of the at least one loop covering member contacts the surface of said fabric; (d) whereby the attached folded end of said at least one loop covering members has a hinge effect on said at least one loop covering member, which serves to causes the loop mating surface of said at least one loop covering member to contact and thereby cover the hook mating surface of said at least one hook closing member.

Alternatively defined most broadly, the present invention is a diaper comprising: (a) a fabric having a surface and an edge; (b) at least one hook closing member having a hook mating surface, where the at least one hook closing member is nonmovably affixed onto the surface of said fabric at a location adjacent to the edge of said fabric, such that the hook mating surface of the at least one hook closing member faces away from the surface of said fabric; and (c) at least one loop covering member having a loop mating surface and an end attached to the surface of said fabric adjacent to said at least one hook closing member, such that the loop mating surface of the at least one loop covering member faces the hook mating surface of the at least one hook closing member, where the at least one loop covering member is made of memory retaining resilient material having spring effect; (d) whereby the spring effect of said memory retaining resilient foam material serves to cause the loop mating surface of said at least one loop covering member to contact and thereby cover the hook mating surface of said at least one hook closing member.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus is intended only for illustration and for disclosure of an operative embodiment and not to show all of the various forms or modification in which the invention might be embodied or operated.

The invention has been described in considerable detail public disclosure of at least one of its forms. However, such detailed description is not intended in any way to limit the broad features or principles of the invention, or the scope of patent monopoly to be granted.

What is claimed is:

1. A diaper cover comprising:
   a. a fabric having a surface and an edge;
   b. a first hook closing member having a hook mating surface, where the first hook closing member is nonmovably affixed onto the surface of said fabric at a first location adjacent to the edge of said fabric, such that the hook mating surface of the first hook closing member faces away from the surface of said fabric;
   c. a second hook closing member having a hook mating surface, where the second hook closing member is nonmovably affixed onto the surface of said fabric at a second location adjacent to the edge of said fabric and remote from said first hook closing member, such that the hook mating surface of the second hook closing member faces away from the surface of said fabric;
   d. a first loop covering member having a loop mating surface and an end attached to the surface of said fabric adjacent to said first hook closing member by a first pair of spaced apart stitch lines, such that the loop mating surface of the first loop covering member faces the hook mating surface of said first hook closing member; and
   e. a second loop covering member having a loop mating surface and an end attached to the surface of said fabric adjacent to said second hook closing member by a second pair of spaced apart stitch lines, such that the loop mating surface of the second loop covering member faces the hook mating surface of the second hook closing member;
   f. whereby said first and second pairs of spaced apart stitch lines have a hinge effect on said first and second loop covering members respectively, which serves to cause the loop mating surface of said first loop covering member to contact and thereby cover the hook mating surface of said first hook closing member, and to cause the loop mating surface of said second loop covering member to contact and thereby cover the hook mating surface of said second hook closing member.

2. A diaper cover in accordance with claim 1 wherein the end of said first loop covering member is attached to the surface of said fabric adjacent to said first hook closing member and remote from the edge of said fabric, and the end of said second loop covering member is attached to the surface of said fabric adjacent to said second hook closing member and remote from the edge of said fabric.

3. A diaper cover in accordance with claim 1 wherein said first and second loop covering members are made of memory retaining resilient foam material having a spring effect, which combined with the hinge effect of said first and second pairs of stitch lines further serves to cause the loop mating surface of said first loop covering member to contact and thereby cover the hook mating surface of said first hook closing member, and to cause the loop mating surface of said second loop covering member to contact and thereby cover the hook mating surface of said second hook closing member.

4. A diaper cover in accordance with claim 3 wherein said memory retaining resilient foam material has a first side and an oppositely disposed second side, where the first side is laminated to have a loop mating surface.

5. A diaper cover in accordance with claim 4 wherein the second side of said memory retaining resilient foam material is laminated to protect said memory retaining resilient foam material from being damaged.

6. A diaper cover in accordance with claim 3 wherein said memory retaining resilient foam material has a first side and an oppositely disposed second side, where the first side is sewn to have a loop mating surface.

7. A diaper cover in accordance with claim 6 wherein the second side of said memory retaining resilient foam material is laminated to protect said memory retaining resilient foam material from being damaged.

8. A diaper cover comprising:
   a. a fabric having a surface and an edge;
   b. a first hook closing member having a hook mating surface, where the first hook closing member is nonmovably affixed onto the surface of said fabric at a first location adjacent to the edge of said fabric, such that the hook mating surface of the first hook closing member faces away from the surface of said fabric;
   c. a second hook closing member having a hook mating surface, where the second hook closing member is nonmovably affixed onto the surface of said fabric at a second location adjacent to the edge of said fabric and remote from said first hook closing member, such that the hook mating surface of the second hook closing member faces away from the surface of said fabric;
   d. a first loop covering member having a loop mating surface and a folded end attached to the surface of said fabric adjacent to said first hook closing member by at least one stitch line, such that the loop mating surface of the first loop covering member faces the hook mating surface of said first hook closing member and the folded end of the first loop covering member contacts the surface of said fabric; and
   e. a second loop covering member having a loop mating surface and a folded end attached to the surface of said fabric adjacent to said second hook closing member by at least one stitch line, such that the loop mating surface of the second loop covering member faces the hook mating surface of said second hook closing member and the folded end of the second loop covering member contacts the surface of said fabric;
   f. whereby the attached folded ends of said first and second loop covering members have a hinge effect on said first and second loop covering members respectively, which serves to cause the loop mating surface of said first loop covering member to contact and thereby cover the hook mating surface of said first hook closing member, and to cause the loop mating surface of said second loop covering member to contact and thereby cover the hook mating surface of said second hook closing member.

9. A diaper cover in accordance with claim 8 wherein the folded end of said first loop covering member is attached to the surface of said fabric adjacent to said first hook closing member and remote from the edge of said fabric, and the folded end of said second loop covering member is attached to the surface of said fabric adjacent to said second hook closing member and remote from the edge of said fabric.

10. A diaper cover in accordance with claim 8 wherein said first and second loop covering members are made of memory retaining resilient foam material having spring effect, which combined with the hinge effect of the attached folded ends of said first and second loop covering members further serves to cause the loop mating surface of said first loop covering member to contact and thereby cover the hook mating surface of said first hook closing member, and to cause the loop mating surface of said second loop covering member to contact and thereby cover the hook mating surface of said second hook closing member.

11. A diaper cover in accordance with claim 10 wherein said memory retaining resilient foam material has a first side and an oppositely disposed second side, where the first side is laminated to have a loop mating surface.

12. A diaper cover in accordance with claim 11 wherein the second side of said memory retaining resilient foam material is laminated to protect said memory retaining resilient foam material from being damaged.

13. A diaper cover in accordance with claim 10 wherein said memory retaining resilient foam material has a first side and an oppositely disposed second side, where the first side is sewn to have a loop mating surface.

14. A diaper cover in accordance with claim 13 wherein the second side of said memory retaining resilient foam material is laminated to protect said memory retaining resilient foam material from being damaged.

15. A diaper cover comprising:
   a. a fabric having a surface and an edge;
   b. a first hook closing member having a hook mating surface, where the first hook closing member is nonmovably affixed onto the surface of said fabric at a first location adjacent to the edge of said fabric, such that the hook mating surface of the first hook closing member faces away from the surface of said fabric;
   c. a second hook closing member having a hook mating surface, where the second hook closing member is nonmovably affixed onto the surface of said fabric at a second location adjacent to the edge of said fabric and remote from said first hook closing member, such that the hook mating surface of the second hook closing member faces away from the surface of said fabric;
   d. a first loop covering member having a loop mating surface and an end attached to the surface of said fabric adjacent to said first hook closing member, such that the loop mating surface of the first loop covering member faces the hook mating surface of said first hook closing member, where the first loop covering member is made of memory retaining resilient material having a spring effect; and
   e. a second loop covering member having a loop mating surface and an end attached to the surface of said fabric adjacent to said second hook closing member, such that the loop mating surface of the second loop covering member faces the hook mating surface of the second hook closing member, where the second loop covering member is made of memory retaining resilient material having spring effect;
   f. whereby the spring effect of said memory retaining resilient foam material serves to cause the loop mating surface of said first loop covering member to contact and thereby cover the hook mating surface of said first hook closing member, and to cause the loop mating surface of said second loop covering member to contact and thereby cover the hook mating surface of said second hook closing member.

16. A diaper cover in accordance with claim 15 wherein the end of said first loop covering member is attached to the surface of said fabric adjacent to said first hook closing member and remote from the edge of said fabric, and the end of said second loop covering member is attached to the surface of said fabric adjacent to said second hook closing member and remote from the edge of said fabric.

17. A diaper cover in accordance with claim 15 wherein said memory retaining resilient material has a first side and an oppositely disposed second side, where the first side is laminated to have a loop mating surface.

18. A diaper cover in accordance with claim 17 wherein the second side of said memory retaining resilient material is laminated to protect said memory retaining resilient foam material from being damaged.

19. A diaper cover in accordance with claim 15 wherein said memory retaining resilient material has a first side and an oppositely disposed second side, where the first side is sewn to have a loop mating surface.

20. A diaper cover in accordance with claim 19 wherein the second side of said memory retaining resilient material is laminated to protect said memory retaining resilient foam material from being damaged.

21. A diaper cover comprising:
 a. a fabric having a surface and an edge;
 b. at least one hook closing member having a hook mating surface, where the at least one hook closing member is nonmovably affixed onto the surface of said fabric at a location adjacent to the edge of said fabric, such that the hook mating surface of the at least one hook closing member faces away from the surface of said fabric; and
 c. at least one loop covering member having a loop mating surface and an end attached to the surface of said fabric adjacent to said at least one hook closing member by a pair of spaced apart stitch lines, such that the loop mating surface of the at least one loop covering member faces the hook mating surface of said at least one hook closing member;
 d. whereby said pair of spaced apart stitch lines has a hinge effect on said at least one loop covering member, which serves to cause the loop mating surface of said at least one loop covering member to contact and thereby cover the hook mating surface of said at least one hook closing member.

22. A diaper cover in accordance with claim 21 wherein the end of said at least one loop covering member is attached to the surface of said fabric adjacent to said at least one hook closing member and remote from the edge of said fabric.

23. A diaper cover in accordance with claim 21 wherein said at least one loop covering member is made of memory retaining resilient foam material having spring effect, which combined with the hinge effect of said pair of stitch lines further serves to cause the loop mating surface of said at least one loop covering member to contact and thereby cover the hook mating surface of said at least one hook closing member.

24. A diaper cover comprising:
 a. a fabric having a surface and an edge;
 b. at least one hook closing member having a hook mating surface, where the at least one hook closing member is nonmovably affixed onto the surface of said fabric at a location adjacent to the edge of said fabric, such that the hook mating surface of the at least one hook closing member faces away from the surface of said fabric; and
 c. at least one loop covering member having a loop mating surface and a folded end attached to the surface of said fabric adjacent to said at least one hook closing member by at least one stitch line, such that the loop mating surface of the at least one loop covering member faces the hook mating surface of said at least one hook closing member and the folded end of the at least one loop covering member contacts the surface of said fabric;
 d. whereby the attached folded end of said at least one loop covering members has a hinge effect on said at least one loop covering member, which serves to cause the loop mating surface of said at least one loop covering member to contact and thereby cover the hook mating surface of said at least one hook closing member.

25. A diaper cover in accordance with claim 24 wherein the folded end of said at least one loop covering member is attached to the surface of said fabric adjacent to said at least one hook closing member and remote from the edge of said fabric.

26. A diaper cover in accordance with claim 24 wherein said at least one loop covering member is made of memory retaining resilient foam material having spring effect, which combined with the hinge effect of said pair of stitch lines further serves to cause the loop mating surface of said at least one loop covering member to contact and thereby cover the hook mating surface of said at least one hook closing member.

27. A diaper cover comprising:
 a. a fabric having a surface and an edge;
 b. at least one hook closing member having a hook mating surface, where the at least one hook closing member is nonmovably affixed onto the surface of said fabric at a location adjacent to the edge of said fabric, such that the hook mating surface of the at least one hook closing member faces away from the surface of said fabric; and
 c. at least one loop covering member having a loop mating surface and an end attached to the surface of said fabric adjacent to said at least one hook closing member, such that the loop mating surface of the at least one loop covering member faces the hook mating surface of the at least one hook closing member, where the at least one loop covering member is made of memory retaining resilient material having a spring effect;
 d. whereby the spring effect of said memory retaining resilient foam material serves to cause the loop mating surface of said at least one loop covering member to contact and thereby cover the hook mating surface of said at least one hook closing member.

28. A diaper cover in accordance with claim 27 wherein the end of said at least one loop covering member is attached to the surface of said fabric adjacent to said at least one hook closing member and remote from the edge of said fabric.

29. A diaper cover comprising:
 a. a fabric having a surface and an edge;
 b. a first loop closing member having a loop mating surface, where the first loop closing member is nonmovably affixed onto the surface of said fabric at a first location adjacent to the edge of said fabric, such that the loop mating surface of the first loop closing member faces away from the surface of said fabric;
 c. A second loop closing member having a loop mating surface, where the second loop closing member is nonmovably affixed onto the surface of said fabric at a second location adjacent to the edge of said fabric and remote from said first loop closing member, such that the loop mating surface of the second loop closing member faces away from the surface of said fabric;

d. a first hook covering member having a hook mating surface and an end attached to the surface of said fabric adjacent to said first loop closing member by a first pair of spaced apart stitch lines, such that the hook mating surface of the first hook covering member faces the loop mating surface of said first loop closing member; and e. a second hook covering member having a hook mating surface and an end attached to the surface of said fabric adjacent to said second loop closing member by a second pair of spaced apart stitch lines, such that the hook mating surface of the second hook covering member faces the loop mating surface of the second loop closing member;

f. whereby said first and second pairs of spaced apart stitch lines have hinge effect on said first and second hook covering members respectively, which serves to cause the hook mating surface of said first hook covering member to contact and thereby cover the loop mating surface of said first loop closing member, and to cause the hook mating surface of said second hook covering member to contact and thereby cover the loop mating surface of said second loop closing member.

30. A diaper cover in accordance with claim 29 wherein the end of said first hook covering member is attached to the surface of said fabric adjacent to said first loop closing member and remote from the edge of said fabric, and the end of said second hook covering member is attached to the surface of said fabric adjacent to said second loop closing member and remote from the edge of said fabric.

31. A diaper cover comprising:
a. a fabric having a surface and an edge;
b. a first loop closing member having a loop mating surface, where the first loop closing member is nonmovably affixed onto the surface of said fabric at a first location adjacent to the edge of said fabric, such that the loop mating surface of the first loop closing member faces away from the surface of said fabric;
c. a second loop closing member having a loop mating surface, where the second loop closing member is nonmovably affixed onto the surface of said fabric at a second location adjacent to the edge of said fabric and remote from said first loop closing member, such that the loop mating surface of the second loop closing member faces away from the surface of said fabric;
d. a first hook covering member having a hook mating surface and a folded end attached to the surface of said fabric adjacent to said first loop closing member by at least one stitch line, such that the hook mating surface of the first hook covering member faces the loop mating surface of said first loop closing member and the folded end of the first hook covering member contacts the surface of said fabric; and
e. a second hook covering member having a hook mating surface and a folded end attached to the surface of said fabric adjacent to said second loop closing member by at least one stitch line, such that the hook mating surface of the second hook covering member faces the loop mating surface of said second loop closing member and the folded end of the second hook covering member contacts the surface of said fabric;

f. whereby the attached folded ends of said first and second hook covering members have a hinge effect on said first and second hook covering members respectively, which serves to cause the hook mating surface of said first hook covering member to contact and thereby cover the loop mating surface of said first loop closing member, and to cause the hook mating surface of said second hook covering member to contact and thereby cover the loop mating surface of said second loop closing member.

32. A diaper cover in accordance with claim 31 wherein the folded end of said first hook covering member is attached to the surface of said fabric adjacent to said first loop closing member and remote from the edge of said fabric, and the folded end of said second hook covering member is attached to the surface of said fabric adjacent to said second loop closing member and remote from the edge of said fabric.

33. A diaper cover comprising:
a. a fabric having a surface and an edge;
b. at least one loop closing member having a loop mating surface, where the at least one loop closing member is nonmovably affixed onto the surface of said fabric at a location adjacent to the edge of said fabric, such that the loop mating surface of the at least one loop closing member faces away from the surface of said fabric; and
c. at least one hook covering member having a hook mating surface and an end attached to the surface of said fabric adjacent to said at least one loop closing member by a pair of spaced apart stitch lines, such that the hook mating surface of the at least one hook covering member faces the loop mating surface of said at least one loop closing member;
d. whereby said pair of spaced apart stitch lines has a hinge effect on said at least one hook covering member, which serves to cause the hook mating surface of said at least one hook covering member to contact and thereby cove the loop mating surface of said at least one loop closing member.

34. A diaper cover in accordance with claim 33 wherein the end of said at least one hook covering member is attached to the surface of said fabric adjacent to said at least one loop closing member and remote from the edge of said fabric.

35. A diaper cover comprising:
a. a fabric having a surface and an edge;
b. at least one loop closing member having a loop mating surface, where the at least one loop closing member is nonmovably affixed onto the surface of said fabric at a location adjacent to the edge of said fabric, such that the loop mating surface of the at least one loop closing member faces away from the surface of said fabric; and
c. at least one hook covering member having a hook mating surface and a folded end attached to the surface of said fabric adjacent to said at least one loop closing member by at least one stitch line, such that the hook mating surface of the at least one hook covering member faces the loop mating surface of said at least one loop closing member and the folded end of the at least one hook covering member contacts the surface of said fabric;

d. whereby the attached folded end of said at least one hook covering member has a hinge effect on said at least one hook covering member, which serves to cause the hook mating surface of said at least one hook covering member to contact and thereby cover the loop mating surface of said at least one loop closing member.

36. A diaper cover in accordance with claim 35 wherein the folded end of said at least one hook covering member is attached to the surface of said fabric adjacent to said at least one loop closing member and remote from the edge of said fabric.

37. A diaper comprising:
   a. a fabric having a surface and an edge;
   b. a first hook closing member having a hook mating surface, where the first hook closing member is nonmovably affixed onto the surface of said fabric at a first location adjacent to the edge of said fabric, such that the hook mating surface of the first hook closing member faces away from the surface of said fabric;
   c. a second hook closing member having a hook mating surface, where the second hook closing member is nonmovably affixed onto the surface of said fabric at a second location adjacent to the edge of said fabric and remote from said first hook closing member, such that the hook mating surface of the second hook closing member faces away from the surface of said fabric;
   d. a first loop covering member having a loop mating surface and an end attached to the surface of said fabric adjacent to said first hook closing member by a first pair of spaced apart stitch lines, such that the loop mating surface of the first loop covering member faces the hook mating surface of said first hook closing member; and
   e. a second loop covering member having a loop mating surface and an end attached to the surface of said fabric adjacent to said second hook closing member by a second pair of spaced apart stitch lines, such that the loop mating surface of the second loop covering member faces the hook mating surface of the second hook closing member;
   f. whereby said first and second pairs of spaced apart stitch lines have hinge effect on said first and second loop covering members respectively, which serves to cause the loop mating surface of said first loop covering member to contact and thereby cover the hook mating surface of said first hook closing member, and to cause the loop mating surface of said second loop covering member to contact and thereby cover the hook mating surface of said second hook closing member.

38. A diaper in accordance with claim 37 wherein the end of said first loop covering member is attached to the surface of said fabric adjacent to said first hook closing member and remote from the edge of said fabric, and the end of said second loop covering member is attached to the surface of said fabric adjacent to said second hook closing member and remote from the edge of said fabric.

39. A diaper in accordance with claim 37 wherein said first and second loop covering members are made of memory retaining resilient foam material having a spring effect, which combined with the hinge effect of said first and second pairs of stitch lines further serves to cause the loop mating surface of said first loop covering member to contact and thereby cover the hook mating surface of said first hook closing member, and to cause the loop mating surface of said second loop covering member to contact and thereby cover the hook mating surface of said second hook closing member.

40. A diaper in accordance with claim 39 wherein said memory retaining resilient foam material has a first side and an oppositely disposed second side, where the first side is laminated to have a loop mating surface.

41. A diaper in accordance with claim 40 wherein the second side of said memory retaining resilient foam material is laminated to protect said memory retaining resilient foam material from being damaged.

42. A diaper in accordance with claim 39 wherein said memory retaining resilient foam material has a first side and an oppositely disposed second side, where the first side is sewn to have a loop mating surface.

43. A diaper in accordance with claim 42 wherein the second side of said memory retaining resilient foam material is laminated to protect said memory retaining resilient foam material from being damaged.

44. A diaper comprising:
   a. a fabric having a surface and an edge;
   b. a first hook closing member having a hook mating surface, where the first hook closing member is nonmovably affixed onto the surface of said fabric at a first location adjacent to the edge of said fabric, such that the hook mating surface of the first hook closing member faces away from the surface of said fabric;
   c. a second hook closing member having a hook mating surface, where the second hook closing member is nonmovably affixed onto the surface of said fabric at a second location adjacent to the edge of said fabric and remote from said first hook closing member, such that the hook mating surface of the second hook closing member faces away from the surface of said fabric;
   d. a first loop covering member having a loop mating surface and a folded end attached to the surface of said fabric adjacent to said first hook closing member by at least one stitch line, such that the loop mating surface of the first loop covering member faces the hook mating surface of said first hook closing member and the folded end of the first loop covering member contacts the surface of said fabric; and
   e. a second loop covering member having a loop mating surface and a folded end attached to the surface of said fabric adjacent to said second hook closing member by at least one stitch line, such that the loop mating surface of the second loop covering member faces the hook mating surface of said second hook closing member and the folded end of the second loop covering member contacts the surface of said fabric;
   f. whereby the attached folded ends of said first and second loop covering members have a hinge effect on said first and second loop covering members respectively, which serves to cause the loop mating surface of said first loop covering member to contact and thereby cover the hook mating surface of said first hook closing member, and to cause the loop mating surface of said second loop covering member to contact and thereby cover the hook mating surface of said second hook closing member.

45. A diaper in accordance with claim 44 wherein the folded end of said first loop covering member is attached to the surface of said fabric adjacent to said first hook closing member and remote from the edge of said fabric, and the folded end of said second loop covering member is attached to the surface of said fabric adjacent to said second hook closing member and remote from the edge of said fabric.

46. A diaper in accordance with claim 44 wherein said first and second loop covering members are made of memory retaining resilient foam material having spring effect, which combined with the hinge effect of the attached folded ends of said first and second loop covering members further serves to cause the loop mating surface of said first loop covering member to contact and thereby cover the hook mating surface of said first hook closing member, and to cause the loop mating surface of said second loop covering member to contact and thereby cover the hook mating surface of said second hook closing member.

47. A diaper in accordance with claim 46 wherein said memory retaining resilient foam material has a first side and an oppositely disposed second side, where the first side is laminated to have a loop mating surface.

48. A diaper in accordance with claim 47 wherein the second side of said memory retaining resilient foam material is laminated to protect said memory retaining resilient foam material from being damaged.

49. A diaper in accordance with claim 46 wherein said memory retaining resilient foam material has a first side and an oppositely disposed second side, where the first side is sewn to have a loop mating surface.

50. A diaper in accordance with claim 49 wherein the second side of said memory retaining resilient foam material is laminated to protect said memory retaining resilient foam material from being damaged.

51. A diaper comprising:
    a. a fabric having a surface and an edge;
    b. a first hook closing member having a hook mating surface, where the first hook closing member is nonmovably affixed onto the surface of said fabric at a first location adjacent to the edge of said fabric, such that the hook mating surface of the first hook closing member faces away from the surface of said fabric;
    c. a second hook closing member having a hook mating surface, where the second hook closing member is nonmovably affixed onto the surface of said fabric at a second location adjacent to the edge of said fabric and remote from said first hook closing member, such that the hook mating surface of the second hook closing member faces away from the surface of said fabric;
    d. a first loop covering member having a loop mating surface and an end attached to the surface of said fabric adjacent to said first hook closing member, such that the loop mating surface of the first loop covering member faces the hook mating surface of said first hook closing member, where the first loop covering member is made of memory retaining resilient material having a spring effect; and
    e. a second loop covering member having a loop mating surface and an end attached to the surface of said fabric adjacent to said second hook closing member, such that the loop mating surface of the second loop covering member faces the hook mating surface of the second hook closing member, where the second loop covering member is made of memory retaining resilient material having spring effect;
    f. whereby the spring effect of said memory retaining resilient foam material serves to cause the loop mating surface of said first loop covering member to contact mating surface of said first loop covering member to contact and thereby cover the hook mating surface of said first hook closing member, and to cause the loop mating surface of said second loop covering member to contact and thereby cover the hook mating surface of said second hook closing member.

52. A diaper in accordance with claim 51 wherein the end of said first loop covering member is attached to the surface of said fabric adjacent to said first hook closing member and remote from the edge of said fabric, and the end of said second loop covering member is attached to the surface of said fabric adjacent to said second hook closing member and remote from the edge of said fabric.

53. A diaper in accordance with claim 51 wherein said memory retaining resilient foam material has a first side and an oppositely disposed second side, where the first side is laminated to have a loop mating surface.

54. A diaper in accordance with claim 53 wherein the second side of said memory retaining resilient material is laminated to protect said memory retaining resilient foam material from being damaged.

55. A diaper in accordance with claim 51 wherein said memory retaining resilient material has a first side and an oppositely disposed second side, where the first side is sewn to have a loop mating surface.

56. A diaper in accordance with claim 55 wherein the second side of said memory retaining resilient material is laminated to protect said memory retaining resilient foam material from being damaged.

57. A diaper comprising:
    a. a fabric having a surface and an edge;
    b. at least one hook closing member having a hook mating surface, where the at least one hook closing member is nonmovably affixed onto the surface of said fabric at a location adjacent to the edge of said fabric, such that the hook mating surface of the at least one hook closing member faces away from the surface of said fabric; and
    c. at least one loop covering member having a loop mating surface and an end attached to the surface of said fabric adjacent to said at least one hook closing member by a pair of spaced apart stitch lines, such that the loop mating surface of the at least one loop covering member faces the hook mating surface of said at least one hook closing member;
    d. whereby said pair of spaced apart stitch lines has a hinge effect on said at least one loop covering member, which serves to cause the loop mating surface of said at least one loop covering member to contact and thereby cover the hook mating surface of said at least one hook closing member.

58. A diaper in accordance with claim 57 wherein the end of said at least one loop covering member is attached to the surface of said fabric adjacent to said at least one hook closing member and remote from the edge of said fabric.

59. A diaper in accordance with claim 57 wherein said at least one loop covering member is made of memory retaining resilient foam material having spring effect, which combined with the hinge effect of said pair of stitch lines further serves to cause the loop mating surface of said at least one loop covering member to contact and thereby cover the hook mating surface of said at least one hook closing member.

60. A diaper comprising:
   a. a fabric having a surface and an edge;
   b. at least one hook closing member having a hook mating surface, where the at least one hook closing member is nonmovably affixed onto the surface of said fabric at a location adjacent to the edge of said fabric, such that the hook mating surface of the at least one hook closing member faces away from the surface of said fabric; and
   c. at least one loop covering member having a loop mating surface and a folded end attached to the surface of said fabric adjacent to said at least one hook closing member by at least one stitch line, such that the loop mating surface of the at least one loop covering member faces the hook mating surface of said at least one hook closing member and the folded end of the at least one loop covering member contacts the surface of said fabric;
   d. whereby the attached folded end of said at least one loop covering members has a hinge effect on said at least one loop covering member, which serves to cause the loop mating surface of said at least one loop covering member to contact and thereby cover the hook mating surface of said at least one hook closing member.

61. A diaper in accordance with claim 60 wherein the folded end of said at least one loop covering member is attached to the surface of said fabric adjacent to said at least one hook closing member and remote from the edge of said fabric.

62. A diaper in accordance with claim 60 wherein said at least one loop covering member is made of memory retaining resilient foam material having spring effect, which combined with the hinge effect of said pair of stitch lines further serves to cause the loop mating surface of said at least one loop covering member to contact and thereby cover the hook mating surface of said at least one hook closing member.

63. A diaper comprising:
   a. a fabric having a surface and an edge;
   b. at least one hook closing member having a hook mating surface, where the at least one hook closing member is nonmovably affixed onto the surface of said fabric at a location adjacent to the edge of said fabric, such that the hook mating surface of the at least one hook closing member faces away from the surface of said fabric; and
   c. at least one loop covering member having a loop mating surface and an end attached to the surface of said fabric adjacent to said at least one hook closing member, such that the loop mating surface of the at least one loop covering member faces the hook mating surface of the at least one hook closing member, where the at least one loop covering member is made of memory retaining resilient material having a spring effect;
   d. whereby the spring effect of said memory retaining resilient foam material serves to cause the loop mating surface of said at least one loop covering member to contact and thereby cover the hook mating surface of said at least one hook closing member.

64. A diaper in accordance with claim 63 wherein the end of said at least one loop covering member is attached to the surface of said fabric adjacent to said at least one hook closing member and remote from the edge of said fabric.

65. A diaper comprising:
   a. a fabric having a surface and an edge;
   b. a first loop closing member having a loop mating surface, where the first loop closing member is nonmovably affixed onto the surface of said fabric at a first location adjacent to the edge of said fabric, such that the loop mating surface of the first loop closing member faces away from the surface of said fabric;
   c. a second loop closing member having a loop mating surface, where the second loop closing member is nonmovably affixed onto the surface of said fabric at a second location adjacent to the edge of said fabric and remote from said first loop closing member, such that the loop mating surface of the second loop closing member faces away from the surface of said fabric;
   d. a first hook covering member having a hook mating surface and an end attached to the surface of said fabric adjacent to said first loop closing member by a first pair of spaced apart stitch lines, such that the hook mating surface of the first hook covering member faces the loop mating surface of said first loop closing member; and
   e. a second hook covering member having a hook mating surface and an end attached to the surface of said fabric adjacent to said second loop closing member by a second pair of spaced apart stitch lines, such that the hook mating surface of the second hook covering member faces the loop mating surface of the second loop closing member;
   f. whereby said first and second pairs of spaced apart stitch lines have hinge effect on said first and second hook covering members respectively, which serves to cause the hook mating surface of said first hook covering member to contact and thereby cover the loop mating surface of said first loop closing member, and to cause the hook mating surface of said second hook covering member to contact and thereby cover the loop mating surface of said second loop closing member.

66. A diaper in accordance with claim 65 wherein the end of said first hook covering member is attached to the surface of said fabric adjacent to said first loop closing member and remote from the edge of said fabric, and the end of said second hook covering member is attached to the surface of said fabric adjacent to said second loop closing member and remote from the edge of said fabric.

67. A diaper comprising:
   a. a fabric having a surface and an edge;
   b. a first loop closing member having a loop mating surface, where the first loop closing member is nonmovably affixed onto the surface of said fabric at a first location adjacent to the edge of said fabric, such that the loop mating surface of the first loop closing member faces away from the surface of said fabric;
   c. a second loop closing member having a loop mating surface, where the second loop closing member is nonmovably affixed onto the surface of said fabric at a second location adjacent to the edge of said fabric and remote from said first loop closing member, such that the loop mating surface of the second loop closing member faces away from the surface of said fabric;

d. a first hook covering member having a hook mating surface and a folded end attached to the surface of said fabric adjacent to said first loop closing member by at least one stitch line, such that the hook mating surface of the first hook covering member faces the loop mating surface of said first loop closing member and the folded end of the first hook covering member contacts the surface of said fabric; and e. a second hook covering member having a hook mating surface and a folded end attached to the surface of said fabric adjacent to said second loop closing member by at least one stitch line, such that the hook mating surface of the second hook covering member faces the loop mating surface of said second loop closing member and the folded end of the second hook covering member contacts the surface of said fabric;

f. whereby the attached folded ends of said first and second hook covering members have a hinge effect on said first and second hook covering members respectively, which serves to cause the hook mating surface of said first hook covering member to contact and thereby cover the loop mating surface of said first loop closing member, and to cause the hook mating surface of said second hook covering member to contact and thereby cover the loop mating surface of said second loop closing member.

68. A diaper in accordance with claim 67 wherein the folded end of said first hook covering member is attached to the surface of said fabric adjacent to said first loop closing member and remote from the edge of said fabric, and the folded end of said second hook covering member is attached to the surface of said fabric adjacent to said second loop closing member and remote from the edge of said fabric.

69. A diaper comprising:

a. a fabric having a surface and an edge;

b. at least one loop closing member having a loop mating surface, where the at least one loop closing member is nonmovably affixed onto the surface of said fabric at a location adjacent to the edge of said fabric, such that the loop mating surface of the at least one loop closing member faces away from the surface of said fabric; and c. at least one hook covering member having a hook mating surface and an end attached to the surface of said fabric adjacent to said at least one loop closing member by a pair of spaced apart stitch lines, such that the hook mating surface of the at least one hook covering member faces the loop mating surface of said at least one loop closing member;

d. whereby said pair of spaced apart stitch lines has a hinge effect on said at least one hook covering member, which serves to cause the hook mating surface of said at least one hook covering member to contact and thereby cover the loop mating surface of said at least one loop closing member.

70. A diaper in accordance with claim 69 wherein the end of said at least one hook covering member is attached to the surface of said fabric adjacent to said at least one loop closing member and remote from the edge of said fabric.

71. A diaper comprising:

a. a fabric having a surface and an edge;

b. at least one loop closing member having a loop mating surface, where the at least one loop closing member is nonmovably affixed onto the surface of said fabric at a location adjacent to the edge of said fabric, such that the loop mating surface of the at least one loop closing member faces away from the surface of said fabric; and c. at least one hook covering member having a hook mating surface and a folded and attached to the surface of said fabric adjacent to said at least one loop closing member by at least one stitch line, such that the hook mating surface of the at least one hook covering member faces the loop mating surface of said at least one loop closing member and the folded end of the at least one hook covering member contacts the surface of said fabric;

d. whereby the attached folded end of said at least one hook covering member has a hinge effect on said at least one hook covering member, which serves to cause the hook mating surface of said at least one hook covering member to contact and thereby cover the loop mating surface of said at least one loop closing member.

72. A diaper in accordance with claim 71 wherein the folded end of said at least one hook covering member is attached to the surface of said fabric adjacent to said at least one loop closing member and remote from the edge of said fabric.

* * * * *